United States Patent
Reynolds et al.

(10) Patent No.: US 7,981,678 B2
(45) Date of Patent: Jul. 19, 2011

(54) SYSTEM AND METHOD FOR AUTOMATIC CALIBRATION

(75) Inventors: Jeffery S. Reynolds, New Fairfield, CT (US); Mu Wu, Hopewell Junction, NY (US); Matthew Holzer, San Francisco, CA (US); Hoi-Cheong Steve Sun, Mount Kisco, NY (US)

(73) Assignee: Bayer Healthcare LLC, Tarrytown, NY (US)

( * ) Notice: Subject to any disclaimer, the term of this patent is extended or adjusted under 35 U.S.C. 154(b) by 366 days.

(21) Appl. No.: 12/129,044

(22) Filed: May 29, 2008

(65) Prior Publication Data

US 2009/0042306 A1 Feb. 12, 2009

Related U.S. Application Data

(60) Provisional application No. 60/954,255, filed on Aug. 6, 2007.

(51) Int. Cl.
*G01N 35/00* (2006.01)
*G01N 27/22* (2006.01)

(52) U.S. Cl. ............. 436/8; 436/63; 436/149; 436/150; 422/82.01; 73/1.01; 73/1.02; 702/122

(58) Field of Classification Search ............... 436/8, 46, 436/63, 95, 149, 150; 435/14; 422/68.1, 422/82.01, 82.02; 73/1.01, 1.02; 702/116, 702/122

See application file for complete search history.

(56) References Cited

U.S. PATENT DOCUMENTS

| | | | |
|---|---|---|---|
| 4,510,383 A | 4/1985 | Ruppender |
| 4,714,847 A | 12/1987 | Harnden et al. |
| 4,929,426 A | 5/1990 | Bodai et al. |
| 4,940,945 A | 7/1990 | Littlejohn et al. |
| 5,194,393 A | 3/1993 | Hugl et al. |
| 5,281,395 A | 1/1994 | Markart et al. |
| 5,379,214 A | 1/1995 | Arbuckle et al. |
| 5,443,080 A | 8/1995 | D'Angelo et al. |
| 5,445,967 A | 8/1995 | Deuter |
| 5,462,064 A | 10/1995 | D'Angelo et al. |
| 5,489,414 A | 2/1996 | Schreiber et al. |
| 5,510,266 A | 4/1996 | Bonner et al. |
| 5,518,689 A | 5/1996 | Dosmann et al. |
| 5,575,403 A | 11/1996 | Charlton et al. |
| 5,580,794 A | 12/1996 | Allen |
| 5,597,532 A | 1/1997 | Connolly |
| 5,611,999 A | 3/1997 | Dosmann et al. |
| 5,780,304 A | 7/1998 | Matzinger et al. |
| 5,795,543 A | 8/1998 | Poto et al. |
| 5,830,133 A | 11/1998 | Osten et al. |
| 5,837,546 A | 11/1998 | Allen et al. |
| 5,856,195 A | 1/1999 | Charlton et al. |
| 5,863,800 A | 1/1999 | Eikmeier et al. |

(Continued)

FOREIGN PATENT DOCUMENTS

EP 0840122 5/1998

(Continued)

*Primary Examiner* — Maureen M Wallenhorst
(74) *Attorney, Agent, or Firm* — Nixon Peabody LLP

(57) ABSTRACT

A device includes a sensor array and a processor is automatically calibrated. The sensor array collects data from a pattern using at least one of a capacitive measurement and a radio frequency measurement. The pattern is included on a calibration storage device. The processor receives the data from the sensor array and calibrates the device in accordance with the data.

26 Claims, 10 Drawing Sheets

U.S. PATENT DOCUMENTS

| | | |
|---|---|---|
| 5,866,349 A | 2/1999 | Lilja et al. |
| 5,945,341 A | 8/1999 | Howard, III |
| 5,962,215 A | 10/1999 | Douglas et al. |
| 5,989,917 A * | 11/1999 | McAleer et al. ............... 436/46 |
| 6,168,957 B1 | 1/2001 | Matzinger et al. |
| 6,335,203 B1 | 1/2002 | Patel et al. |
| 6,377,894 B1 | 4/2002 | Deweese et al. |
| 6,441,898 B1 | 8/2002 | Markart |
| 6,485,437 B1 | 11/2002 | Tapper |
| 6,599,406 B1 | 7/2003 | Kawanaka et al. |
| 6,645,359 B1 | 11/2003 | Bhullar et al. |
| 6,662,439 B1 | 12/2003 | Bhullar |
| 6,767,440 B1 | 7/2004 | Bhullar et al. |
| 6,770,487 B2 | 8/2004 | Crosby |
| 6,773,671 B1 | 8/2004 | Lewis et al. |
| 6,814,844 B2 * | 11/2004 | Bhullar et al. ............ 204/403.01 |
| 6,827,829 B2 | 12/2004 | Kawanaka et al. |
| 6,875,327 B1 | 4/2005 | Miyazaki et al. |
| 2001/0023324 A1 | 9/2001 | Pronovost et al. |
| 2001/0039057 A1 | 11/2001 | Douglas et al. |
| 2001/0045355 A1 | 11/2001 | Gephart et al. |
| 2002/0059030 A1 | 5/2002 | Otworth et al. |
| 2002/0082797 A1 | 6/2002 | Deweese et al. |
| 2002/0133080 A1 | 9/2002 | Apruzzese et al. |
| 2002/0137059 A1 | 9/2002 | Wu et al. |
| 2003/0013941 A1 | 1/2003 | Cohn et al. |
| 2003/0023187 A1 | 1/2003 | Tapper |
| 2003/0040682 A1 | 2/2003 | Tapper |
| 2003/0062262 A1 | 4/2003 | Mansouri et al. |
| 2003/0098233 A1 | 5/2003 | Kermani et al. |
| 2003/0109777 A1 | 6/2003 | Kloepfer et al. |
| 2003/0157726 A1 | 8/2003 | Blum et al. |
| 2003/0191415 A1 | 10/2003 | Moerman et al. |
| 2003/0207441 A1 | 11/2003 | Eyster et al. |
| 2003/0207454 A1 | 11/2003 | Eyster et al. |
| 2004/0012676 A1 | 1/2004 | Weiner et al. |
| 2004/0019653 A1 | 1/2004 | Debaty et al. |
| 2004/0019686 A1 | 1/2004 | Toyoda et al. |
| 2004/0047764 A1 | 3/2004 | Purcell |
| 2004/0106858 A1 | 6/2004 | Say et al. |
| 2004/0156832 A1 | 8/2004 | Jolly |
| 2004/0171921 A1 | 9/2004 | Say et al. |
| 2004/0200720 A1 | 10/2004 | Musho et al. |
| 2004/0200721 A1 | 10/2004 | Bhullar et al. |
| 2004/0244151 A1 | 12/2004 | Sakata et al. |
| 2004/0259180 A1 | 12/2004 | Burke et al. |
| 2005/0016845 A1 | 1/2005 | Groll et al. |
| 2005/0016846 A1 | 1/2005 | Groll et al. |
| 2005/0019805 A1 | 1/2005 | Groll |
| 2005/0019945 A1 | 1/2005 | Groll et al. |
| 2005/0019953 A1 | 1/2005 | Groll |
| 2005/0023137 A1 | 2/2005 | Bhullar et al. |
| 2005/0027181 A1 | 2/2005 | Goode, Jr. et al. |
| 2005/0057676 A1 | 3/2005 | Weiner et al. |
| 2005/0076845 A1 | 4/2005 | Langdale |
| 2005/0079945 A1 | 4/2005 | Wittkopp |
| 2005/0103624 A1 | 5/2005 | Bhullar et al. |
| 2005/0121322 A1 | 6/2005 | Say et al. |
| 2005/0137471 A1 | 6/2005 | Haar et al. |
| 2005/0142033 A1 | 6/2005 | Glezer et al. |
| 2005/0154271 A1 | 7/2005 | Rasdal et al. |
| 2005/0161345 A1 | 7/2005 | Groll et al. |
| 2005/0177072 A1 | 8/2005 | Kloepfer et al. |
| 2005/0196747 A1 | 9/2005 | Stiene |
| 2005/0199494 A1 | 9/2005 | Say et al. |
| 2005/0226846 A1 | 10/2005 | Umlauf et al. |
| 2005/0279647 A1 | 12/2005 | Beaty |
| 2006/0042964 A1 | 3/2006 | Mansouri et al. |
| 2006/0091006 A1 | 5/2006 | Wang et al. |
| 2006/0108218 A1 | 5/2006 | Gephart et al. |
| 2006/0189895 A1 | 8/2006 | Neel et al. |
| 2006/0271307 A1 | 11/2006 | Huang |
| 2007/0110615 A1 | 5/2007 | Neel et al. |
| 2007/0212258 A1 * | 9/2007 | Neel et al. ................. 422/58 |
| 2007/0259431 A1 | 11/2007 | Charlton et al. |
| 2007/0273904 A1 | 11/2007 | Robinson et al. |
| 2008/0105024 A1 | 5/2008 | Creaven et al. |
| 2008/0190766 A1 * | 8/2008 | Rush et al. .................... 204/400 |
| 2009/0030617 A1 | 1/2009 | Schell et al. |
| 2009/0113981 A1 | 5/2009 | Beer |
| 2009/0125268 A1 | 5/2009 | Perry |
| 2009/0205399 A1 | 8/2009 | Sun et al. |
| 2009/0288964 A1 | 11/2009 | Jung et al. |
| 2009/0326355 A1 * | 12/2009 | Brenneman et al. .......... 600/347 |
| 2010/0084466 A1 * | 4/2010 | Charlton et al. ............. 235/451 |

FOREIGN PATENT DOCUMENTS

| | | |
|---|---|---|
| EP | 1024358 | 8/2000 |
| EP | 1152239 | 11/2001 |
| EP | 1256798 | 11/2002 |
| EP | 1 288 653 | 3/2003 |
| EP | 1288653 | 3/2003 |
| EP | 1431758 | 6/2004 |
| EP | 1475630 | 11/2004 |
| EP | 1 484 603 | 12/2004 |
| EP | 1484603 | 12/2004 |
| EP | 1593961 | 11/2005 |
| EP | 1666605 | 6/2006 |
| JP | 2000/019147 | 1/2000 |
| WO | WO 01/73420 | 10/2001 |
| WO | WO 03/019165 | 3/2003 |
| WO | WO 2004/113911 | 12/2004 |
| WO | WO 2004/113914 | 12/2004 |
| WO | WO 2004/113915 | 12/2004 |
| WO | WO 2005/001474 | 1/2005 |
| WO | 2006/026741 | 3/2006 |
| WO | WO 2006/035322 | 4/2006 |
| WO | WO 2006/042304 A1 | 4/2006 |
| WO | WO 2006/113723 | 10/2006 |
| WO | WO 2006/113865 | 10/2006 |
| WO | WO 2007/078533 | 7/2007 |
| WO | WO 2007/100651 | 9/2007 |
| WO | WO 2008/057479 | 5/2008 |

* cited by examiner

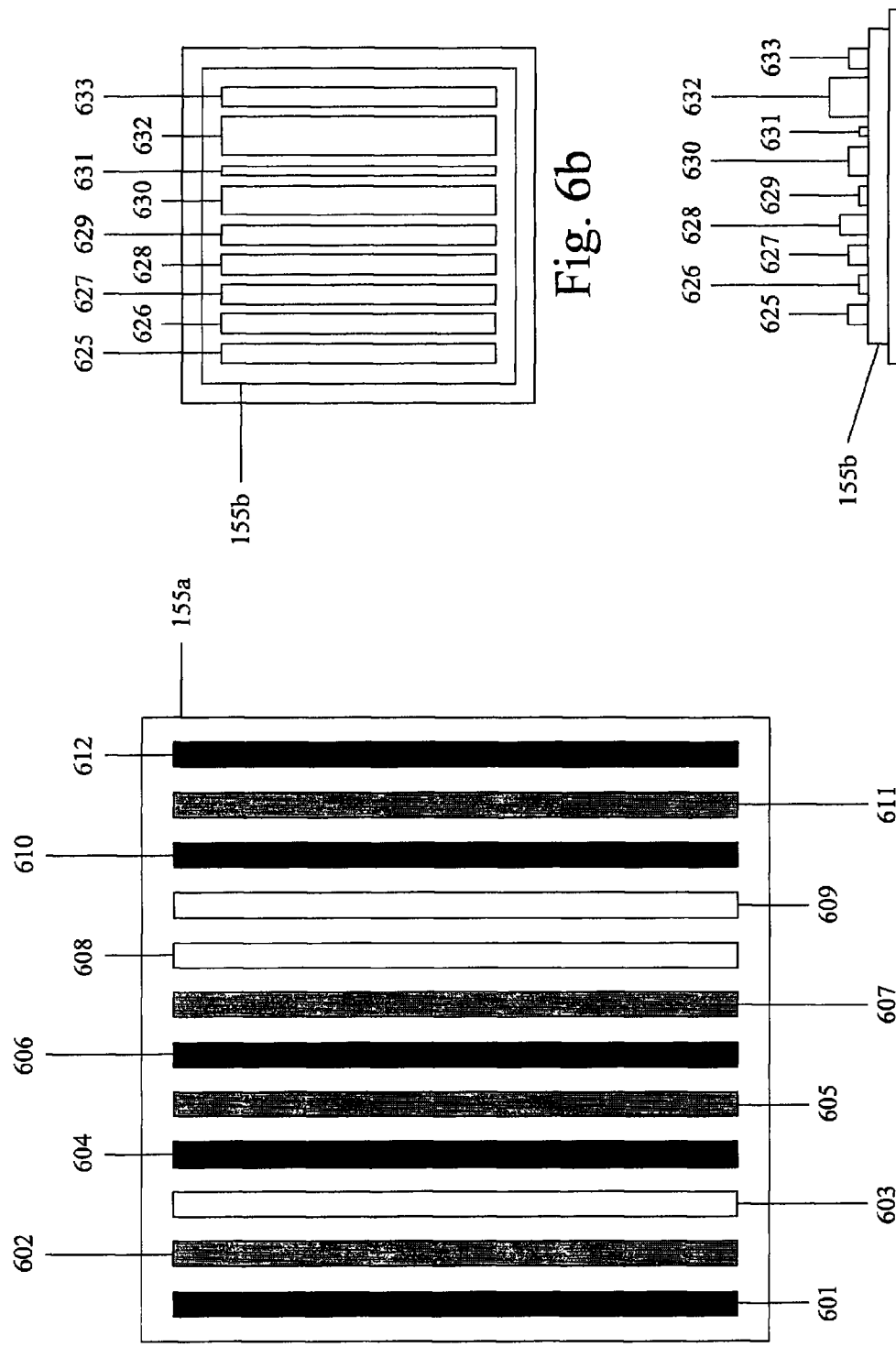

SYSTEM AND METHOD FOR AUTOMATIC CALIBRATION

PRIORITY CLAIM

This application claims the priority to the U.S. Provisional Application Ser. No. 60/954,255, entitled "System and Method for Automatic Calibration," filed Aug. 6, 2007. The specification of the above-identified application is incorporated herewith by reference.

FIELD OF THE INVENTION

The present invention relates generally to automatically calibrating a device. Specifically, the calibration may be accomplished using a capacitive or radio frequency sensor scanning encoded data.

BACKGROUND

Electronic devices may have to be set up or calibrated in order to properly perform a desired functionality. In certain instances, the electronic devices may have to be calibrated each time the functionality is accessed or used. For example, blood glucose meters (BGMs) may be used to test an amount of glucose that is in a person's blood. Each time an individual uses the BGM device, the BGM device may have to be calibrated in order to provide the user with correct and accurate results.

SUMMARY OF THE INVENTION

The present invention relates to a device comprising a sensor array and a processor. The sensor array collects data from a pattern using at least one of a capacitive measurement and a radio frequency measurement. The pattern is included on a calibration storage device. The processor receives the data from the sensor array and calibrates the device in accordance with the data.

DESCRIPTION OF THE DRAWINGS

FIG. 6a shows a top view of a first exemplary pattern according to an exemplary embodiment of the present invention.

FIG. 6b shows a top view of a second exemplary pattern according to an exemplary embodiment of the present invention.

FIG. 6c shows a side view of the second exemplary pattern of FIG. 6b.

DETAILED DESCRIPTION

Figure 1:
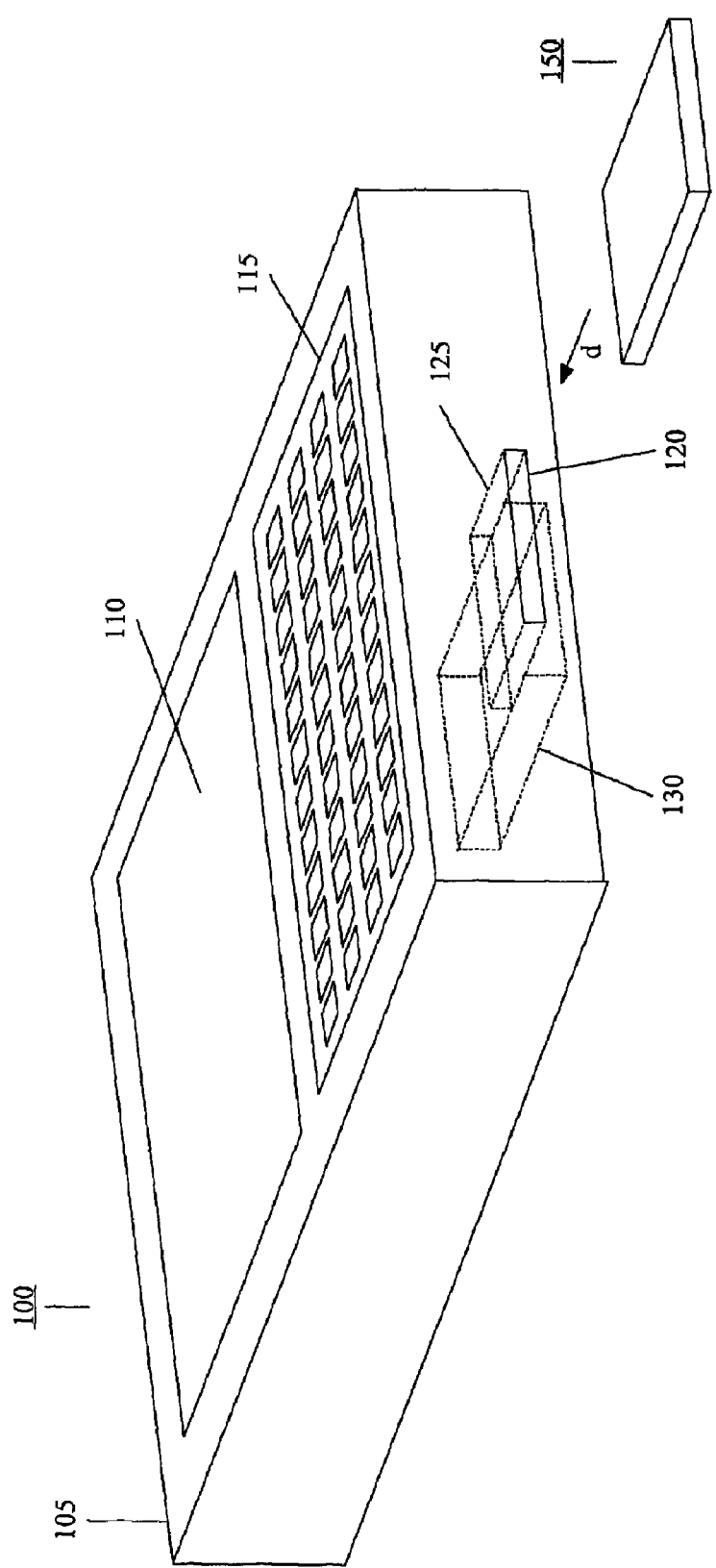
FIG. 1 shows a perspective view of a device and a calibration storage device according to an exemplary embodiment of the present invention.

The exemplary embodiments of the present invention may be further understood with reference to the following description and the appended drawings, wherein like elements are referred to with the same reference numerals. The exemplary embodiments of the present invention describe a system and method for calibration of an electronic device. The electronic device in the exemplary embodiments may be a blood glucose meter (BGM). However, those skilled in the art will understand that any type of electronic device may be calibrated according to the exemplary embodiments of the present invention. According to the exemplary embodiments of the present invention, the calibration of the electronic device may be performed using a capacitive or radio frequency (RF) measurement. Furthermore, according to the exemplary embodiments of the present invention, the calibration may be performed automatically. The automatic calibration, capacitive measurement, and the RF measurement will be described in detail below.

It should be noted that the term "calibration" may be used in a conventional sense. That is, the term "calibration" may be used to describe a process to set a plurality of parameters of the electronic device in preparation for a particular function. For example, with a BGM, the parameters may include a lot number, parameters pertaining to conversion of measured signals to glucose concentrations, reagent manufacturing dates, reagent expiration dates, regional specific information, anti-counterfeiting codes, commercial data, software control data, etc. However, it should be noted that the term "calibration" may also be used to generally describe a process where data is received by the electronic device and utilized in preparation to execute a functionality of the device. It should also be noted that the term "glucose" may be used generally to represent an analyte. Thus, the below described exemplary embodiments may be used for any form of analyte such as glucose. Accordingly, the BGM may be used to generally represent an analyte meter.

FIG. 1 shows a perspective view of an electronic device 100 and a calibration storage device 150 according to an exemplary embodiment of the present invention. The device 100 may include a housing 105, a display 110, a data input arrangement 115, a port 120, and a sensor array 130. As discussed above, the device 100 may be any electronic device such as a BGM. The calibration storage device 150 may be insertable into the device 100. The calibration storage device 150 may be a device that holds data so that the device 100 may receive the data. For example, the calibration storage device 150 may be a measurement strip, a glucose strip or strip cartridge for a BGM. The calibration storage device 150 will be discussed in detail below with reference to FIGS. 2, 3, 6a-c, and 7.

The housing 105 may provide a covering for the components of the device 100. The components of the device 100 may be at least partially disposed within the housing 105. For example, the device 100 may include a processor (not shown) that may be wholly disposed within the housing 105. In another example, the device 100 may include an antenna (not shown) to enable wireless communications. The antenna may be partially disposed within the housing 105 while also partially disposed outside the housing 105.

The display 110 may provide a graphical user interface (GUI). The display 110 may show data regarding functionalities performed by the device 100 to a user. The display 110 may be, for example, a liquid crystal display (LCD). Furthermore, the display 110 may be equipped to receive inputs. That is, the display 110 may be a touch screen allowing a user to contact an area of the display 110 that subsequently transmits a signal to the processor.

The data input arrangement 115 may provide the user with an interface to input data. For example, the data input arrangement 115 may be a key pad. The key pad may be arranged in conventional methods such as in alphabetical order, QWERTY format, etc. The data input arrangement 115 may also include a navigation device such as a touch pad, a mouse, etc. It should be noted that the data input arrangement 115 being disposed on a single surface of the housing 105 is only exemplary. Those skilled in the art will understand that the data input arrangement 115 may be disposed on a different surface of the housing 105, multiple surface of the housing 105, etc.

The port 120 may serve as an access site in which another component may be received by the device 100. For example, the port 120 may be used to receive the calibration storage device 150. The calibration storage device 150 may be inserted into the port 120 by moving in a direction d. Upon reception, the calibration storage device 150 may enter a recess 125. The port 120 or the recess 125 may be equipped with locking mechanisms (not shown) that couple with the calibration storage device 150, thereby holding the calibration storage device 150 stationary. It is noted that including the sensor array 130 in the recess 125 and having access via the port 120 is only exemplary. Other arrangements are also possible such as different shaped recesses and/or ports, including the sensor array on an external surface of the device, etc. It may also be possible to include the sensor array 130 as an external device that is connected via a data port to the processor of the device 100. That is, current devices 100 that do not include a sensor array 130, but do include a data port (e.g., an electrical connector to which a plug or other connection from an external device is accepted) may be retrofitted with the sensor array 130.

The sensor array 130 may include a plurality of sensors to receive the data of the calibration storage device 150 upon reception into the port 120 via the recess 125. The plurality of sensors may be used to receive a variety of data available on the calibration storage device 150. However, it should be noted that the sensor array 130 including a plurality of sensors is only exemplary. The calibration storage device 150 may include a single type of data read by one sensor. Thus, the sensor array 130 may include one or more sensors to receive the data available on the calibration storage device 150.

The sensor array 130 may be an array of electrically excited pads on a substrate that may generate an electromagnetic field pattern above the substrate. The electromagnetic field at any frequency of electrical excitation may be modified by changes or non-uniformities in the electrical properties of surrounding materials. By electrically sensing the changes in electrical fields at the array of pads, an image of the electrical properties may be reconstructed. The sensing may be performed by, for example, measuring changes in capacitance or coupled RF fields. The changes may be due to changes in dielectric constant or conductivity. In another embodiment, the sensor array 130 may interpret data from a plurality of sense pads in which at least one sense pad couples to a coding pad. As will be described in detail below, a resulting reading of capacitive data may be used.

A capacitive or radio frequency (RF) measurement may be used to read the dielectric and/or conductive pattern. Upon measuring the pattern, an image or data may be collected. Integrated circuit sensor arrays may be used to measure the capacitance or RF field. The arrays may scan the pattern over a one-dimensional array (thereby scanning the pattern), a two-dimensional sensor (thereby creating an area image), a three-dimensional sensor (thereby creating a solid image). The arrays may also determine capacitance data from a pairing/non-pairing of sense pads with coding pads. The arrays may be designed to read dense data and have a resolution in the range of 250-500 dots per inch (dpi). Thus, a relatively large amount of data may be available in a small area.

With capacitance measurements, an array of small conductive pads on an insulating substrate may be used to measure the mutual capacitance between adjacent pads. The capacitance between the pads may be affected by the dielectric constant of the material directly above and between the pads. A higher dielectric material may yield a higher measured capacitance between the adjacent pads. The capacitance measurement may be made using conventional measuring devices and associated methods. By measuring the map of the capacitance, an image of valleys and ridges may be created. An embodiment of the conductive pads and the resulting capacitance measurements will be described in detail below with reference to FIGS. 7a-b, 8, and 9.

In addition, an RF sensing approach may be used by sensing changes in the electrical properties of an object and its surface. An emitted RF signal may interact with the material that is disposed above it. Some of the RF energy may be reflected back to a receiving antenna on the same substrate. Different materials may cause different reflected RF signals which may then be used to create an image of the material above the sensor array. The material above the array of the emitter antennas and detector antennas on the substrate may also considered as interacting with the antennas' near-field electromagnetic field. Changes in electromagnetic properties such as the dielectric permittivity or constant above the array may affect the field coupled between the antenna pads. Creating a map of the coupled field or reflected field strengths and/or phases may create a map of the material above the array.

The sensor array 130 may be used for capacitive and/or RF measurements. The sensor array 130 may scan/read the data on the calibration storage device 150. The data on the calibration storage device 150 may be encoded using capacitive and/or RF methods. The types of capacitive and/or RF methods will be discussed in detail below with reference to FIGS. 6a-c, 7a-b, 8, 9, and 10.

Therefore, the exemplary embodiments of the present invention may utilize capacitance and/or RF signals as a means for calibration. That is, capacitance and/or RF signals may be used to scan/read a pre-formed object, determine capacitance pairing/non-pairing data, etc. In the case of a conductive pattern or when there is a conductive surface available on the substrate holding the calibration pattern such as a sensor (e.g., BGM), the conductive surface may be connected to a calibration circuit as an excitation electrode (when capacitive) or excitation antenna (when RF).

Figure 2:
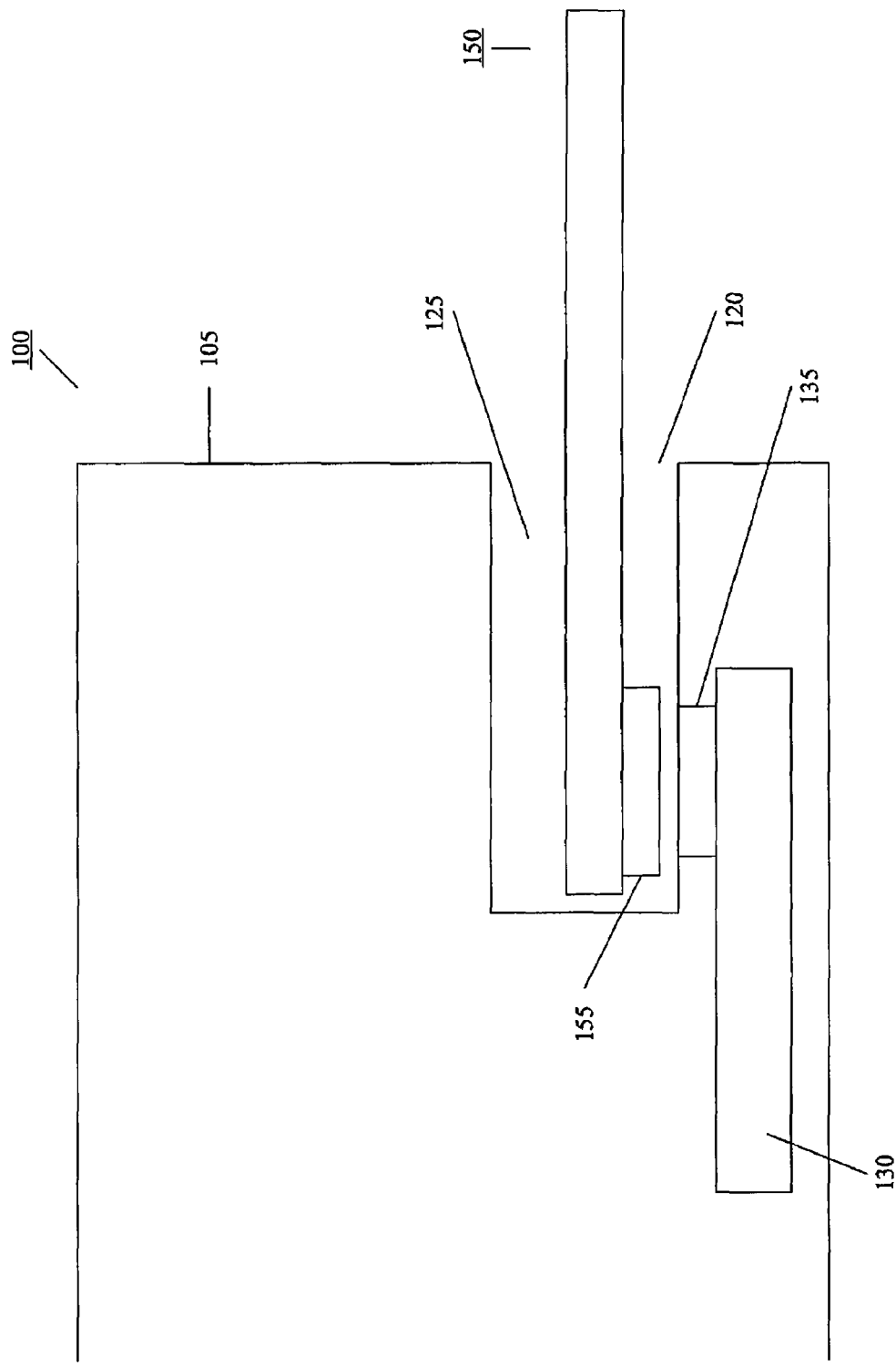
FIG. 2 shows a cross sectional view of the calibration storage device inserted into the device of FIG. 1.

FIG. 2 shows a cross sectional view of the calibration storage device 150 inserted into the device 100 of FIG. 1. The cross sectional view of FIG. 2 includes substantially similar components as described above with respect to the perspective view of FIG. 1. For example, the housing 105 contains the sensor array 130. The port 120 and the recess 125 are also shown. In addition, the cross sectional view further shows a sensing area 135 of the sensor array 130 and a pattern 155 of the strip 150.

Figure 10:
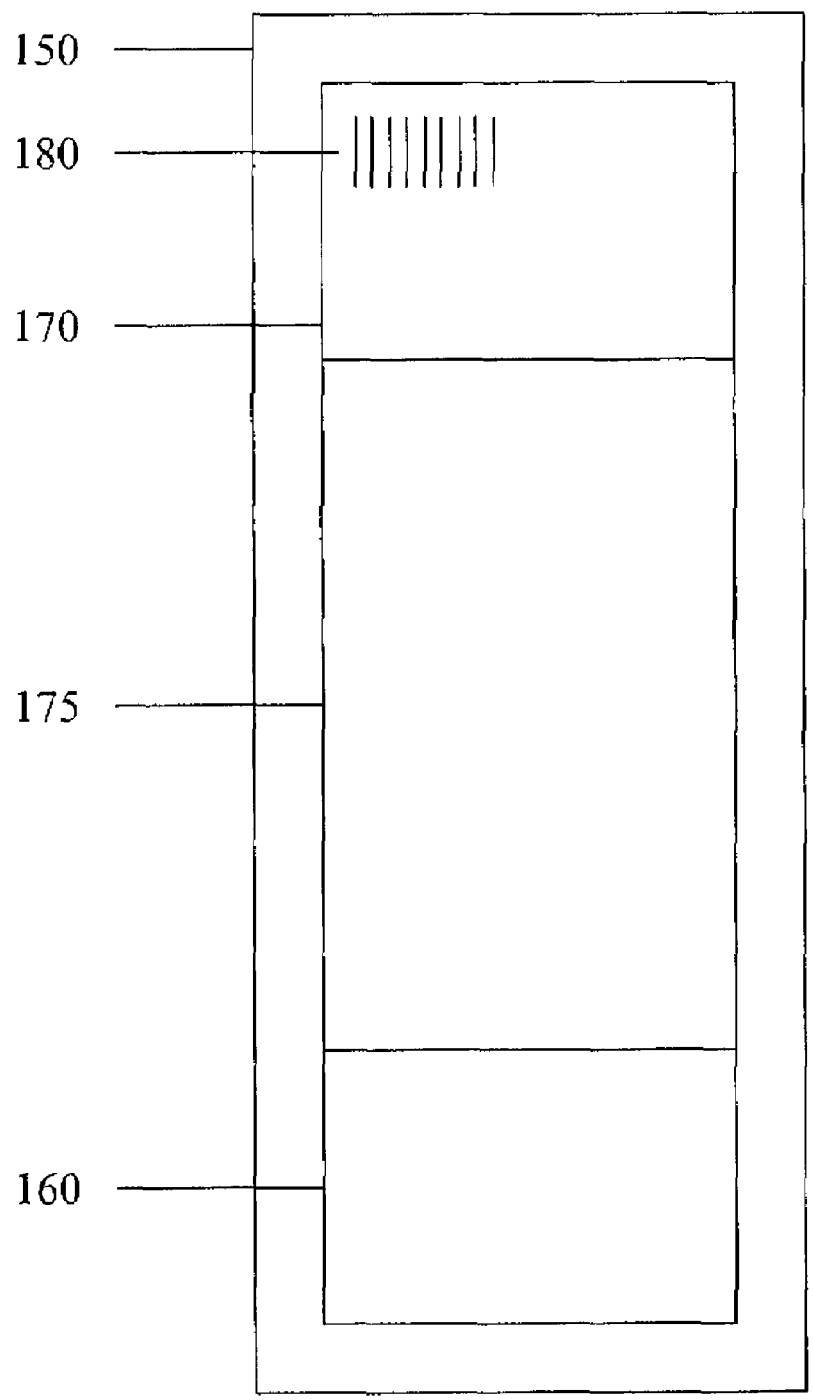
FIG. 10 shows a top view of a fourth exemplary pattern according to an exemplary embodiment of the present invention.

The sensing area 135 of the sensor array 130 is the location at which the pattern 155 of the strip 150 is scanned/read. The sensor array 130 may include circuitry to carry out the scan/read. As shown, the sensing area 135 is located on a periphery of the housing 105 within the recess 125. It should be noted that the sensing area 135 may include a homogeneous or heterogeneous cover made of, for example, glass, polymer, ceramic, or a combination thereof. In the heterogeneous cover, the dielectric material may be patterned to enhance data recovery by concentrating electric field lines to the sensing area 135 above sense pads. For example, the dielectric material may be patterned with air gaps disposed between the sense pads. The cover may serve to protect the sensing area 135 and the sensor array 130. It should be noted that the sensing area 135 located on a bottom side of the recess 125 is only exemplary. Those skilled in the art will understand that depending on the location of the pattern 155 of the calibration storage device 150, the sensing area 135 may be disposed anywhere on a periphery of the recess 125. For example, the pattern 155 may be disposed on a top surface of the calibration storage device 150 such as shown in FIG. 10. Consequently, the sensing area 135 may be located on a top periphery of the recess 125. As discussed above and as will be described in an embodiment below, the sensor array 130 at the sensing area 135 may include a plurality of sensing pads that couple to coding pads of the pattern 155. The sensing array 130 may determine capacitance data and interpret the data or forward the data to a processor. If the sensing array 130 interprets the data, the sensor array 130 may include, for example, an integrated circuit (IC), a processor (e.g., microprocessor), etc.

It should be noted that the pattern 155 being disposed on the calibration storage device 150 is only exemplary. That is, the pattern 155 may be disposed on any location in which the sensing array 130 may scan. For example, the pattern 155 may be disposed on a periphery of a packaging for the device 100. In another example, the pattern 155 may be disposed on a cassette in which the calibration storage device 150 is stored prior to use. Consequently, the sensing array 130 may include a line of sight toward a periphery of the housing 105 in order to scan the pattern 155. In another example, the pattern 155 may be disposed on a side of a packaging for the calibration storage device 150. That is, the calibration of the device 100 may be specific to the calibration storage device 150. Thus, the pattern 155 may be specific to the calibration storage device 150. The sensing array 130 may also include the line of sight toward the periphery of the housing 105. In yet another example, the pattern 155 may be disposed on or in a user manual. That is, the pattern 155 may be on a cover of the user manual, on a page of a section of the user manual, etc. Multiple patterns 155 may be included to correspond to the different types of calibration for the different types of calibration storage devices 150. The sensing array 130 may also include the line of sight toward a periphery of the housing 105 to scan the pattern 155.

It should also be noted that the use of a single pattern 155 is only exemplary. That is, multiple patterns may be used for different types of calibration. The different types of calibration may include, for example, calibrating the device 100 with factory standards, calibrating the device 100 specific to the calibration storage device 150, etc. Thus, the multiple patterns may be disposed on any of the surfaces and in any combination described above such as the calibration storage device 150, the packaging of the device 100, the packaging of the calibration storage devices 150, the user manual, etc. Specifically, the pattern 155 may be specific to each of the calibration storage device 150 such as the case of a dispensing storage device. It should also be noted that a same pattern 150 may be disposed on the various surfaces described above. The repeated disposition of the pattern 150 may serve, for example, as a backup if a pattern disposed on the packaging is damaged. In another example, the same pattern 155 may apply to each of the calibration storage devices 150 such as the case of a canister containing the calibration storage devices 150.

FIG. 6a shows a top view of a first exemplary pattern 155a according to an exemplary embodiment of the present invention. The pattern 155a may be applied to the calibration storage device 150. That is, the pattern 155a is an example of the pattern 155 that may be located on the calibration storage device 150. The pattern 155a includes a plurality of bars 601-612. For example, the bars 601, 604, 606, 610, and 612 may have the same conductance and/or dielectric permittivity; the bars 602, 605, 607, and 611 may have the same conductance and/or dielectric permittivity; and bars 603, 608, and 609 may have the same conductance and/or dielectric permittivity, thereby creating a pattern. The varying contrasts may be accomplished using, for example, a printable material or a patterned thin film material. The varying contrasts may be used to modulate electrical properties relative to the calibration storage device 150. For example, the contrasts may be used to change a relative conductance and/or dielectric permittivity. Thus, when the sensor array 130 is a capacitance sensor, an electromagnetic field passed through the pattern 155a may generate a unique image/scan. The resulting image/scan may be used for calibration purposes. It should be noted that the plurality of bars 601-612 exhibiting different degrees of darkness is only exemplary to illustrate the relative conductance and/or dielectric permittivity. Those skilled in the art will understand that although the bars 601-612 may have varying conductance and/or dielectric permittivity, a visual appearance of the bars 601-612 may be identical.

FIG. 6b shows a top view of a second exemplary pattern 155b according to an exemplary embodiment of the present invention. The pattern 155b may be applied to the calibration storage device 150. That is, the pattern 155b is another example of the pattern 155 that may be located on the calibration storage device 150. The pattern 155b includes a plurality of bars 625-633. The bars 625-633 include varying widths. In this exemplary embodiment, a physical characteristic (i.e., width) is used. For example, bars 625-629 and 633 have a medium width. Bars 630 and 632 have a large width. Bar 631 has a small width. The varying widths may be accomplished using, for example, ink or any other printable material, three dimensional shapes formed from polymers, etched metal or semiconductor, etc. When the sensor array 130 is a capacitance sensor, an electromagnetic field passed through the pattern 155b may generate a unique image/scan. The resulting image/scan may be used for calibration purposes. The varying widths may also be used when the sensor array 130 is an RF sensor. That is, the RF signal that is generated may have varying fluctuations when reflected. For example, the wider bars 630 and 632 have a wide reflection of the RF signal while the small width of bar 631 has a thin reflection. It should be noted that the characteristics (i.e., width) of the pattern 155b may be incorporated into the pattern 155a of FIG. 6a. It should also be noted that the characteristics (i.e., contrast) of the pattern 155a may be incorporated into the pattern 155b.

FIG. 6c shows a side view of the second exemplary pattern 155b of FIG. 6b. FIG. 6c again shows the plurality of bars 625-633. In this exemplary embodiment, the bars 625-633 include varying widths and varying lengths. As discussed above with reference to FIG. 6b, the widths of the bars 625-633 are consistent with the above description. However, it should be noted that the widths may be different from the above description, may all be the same, etc. Bars 625, 627, 630, and 633 have a medium height. Bar 628 has a high height with bar 632 having a highest height. Bar 626, 629, and 631 have a short height. The varying heights may be accomplished using, for example, ink or any other printable material, three dimensional shapes formed from polymers, etched metal or semiconductor, etc. When the sensor array 130 is a capacitance sensor, an electric current passed through the pattern 155b may generate a unique image/scan. The resulting image/scan may be used for calibration purposes. The varying heights may also be used when the sensor array 130 is an RF sensor. That is, the RF signal that is generated may have varying fluctuations when reflected. For example, with near field measurements, the varying heights may produce varying signal strengths upon reflection. It should be noted that the characteristics (i.e., height) of the pattern 155b may be incorporated into the pattern 155a of FIG. 6a. It should also be noted that the characteristics (i.e., contrast) of the pattern 155a may be incorporated into the pattern 155b.

It should be noted that the physical characteristics (i.e., height, width, or a combination thereof) of the pattern 155b may be created using a variety of methods. For example, the height and/or widths may be pre-molded, punched, stamped, etched, laser scribed, etc. In particular, with electrochemical sensors, the conductive pattern already present may be modified by, for example, laser ablation to create the pattern. The pattern may be formed in a way that does not significantly alter the electrical sensing properties of the sensor but still creates a readable calibration pattern. Furthermore, it should be noted that the height and/or widths of the pattern 155b may be inverted. That is, the varying heights and/or widths may be created into the calibration storage device 150, as opposed to being created as an extension of a portion of the surface of the calibration storage device 150. In addition, the varying heights/widths may be a combination of extensions and cavities.

Those skilled in the art will understand that the patterns 155a-b are only exemplary. The patterns 155a-b substantially resemble a bar code when viewed from a top perspective. Thus, the patterns 155a-b may also exhibit the characteristics of bar codes. For example, bar codes may be encoded one-dimensionally, two-dimensionally, three-dimensionally, etc. The patterns 155a-b substantially resemble one-dimensional bar codes. However, the patterns 155a-b may also substantially resemble two-dimensional bar codes or three-dimensional bar codes. That is, for example, the sensor array 130 may scan/read the pattern to generate an image corresponding to the two-dimensional pattern on the calibration storage device 150. Furthermore, the pattern 155 may substantially exhibit both one-dimensional, two-dimensional, and/or three dimensional bar codes.

In addition, the use of bar codes is only exemplary, specifically with respect to two-dimensional bar codes. That is, the two-dimensional bar code may represent any two-dimensional calibration pattern. Thus, a two-dimensional calibration pattern may be used as the patterns 155a-b. For example, a two-dimensional calibration pattern may be slid relative to and perpendicular to an axis of a one-dimensional sensor array so that the two-dimensional calibration pattern may be read. The same may be applied with three-dimensional bar codes.

The above examples illustrated with reference to FIGS. 6a-c show a type of pattern 155 in which the sensing array 130 scans/reads the data contained therein. That is, the sensing array 130 may be generic to read any type of pattern that contains capacitive and/or RF data. In another embodiment, as discussed above, the sensor array 130 may include a plurality of sense pads in which at least one sense pad may couple to a coding pad of the pattern 155. That is, the sensing array 130 may be specific to read a corresponding type of pattern. Furthermore, the coupling of the sense pad with a coding pad or a non-coupled sense pad may produce capacitance data used for calibration purposes.

Figure 7A:
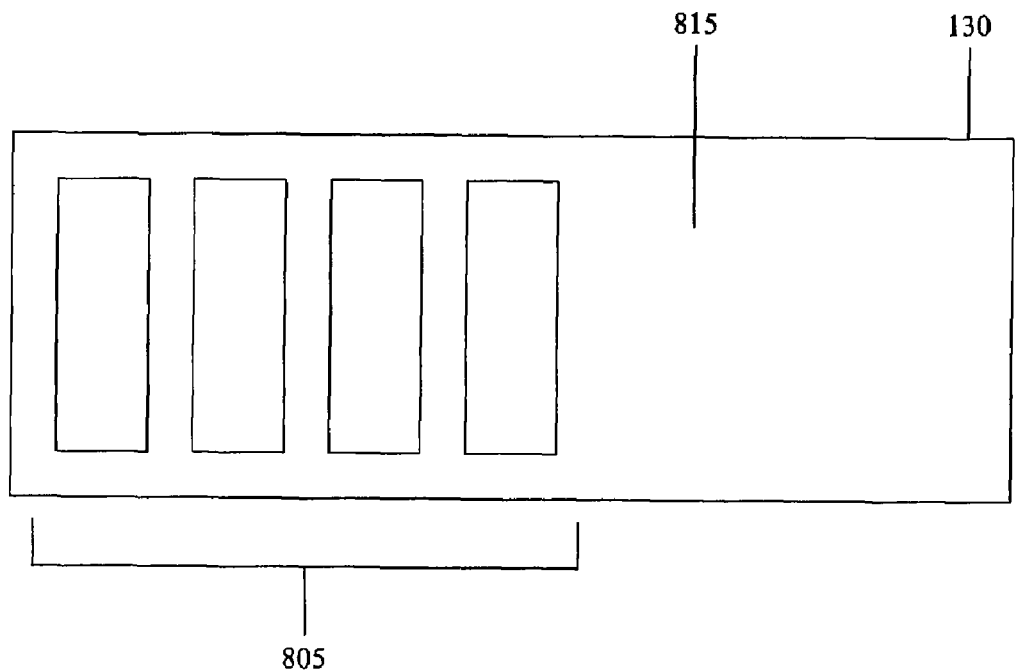
FIG. 7a shows a top view of sense pads of a sensor array according to an exemplary embodiment of the present invention.
Figure 7B:
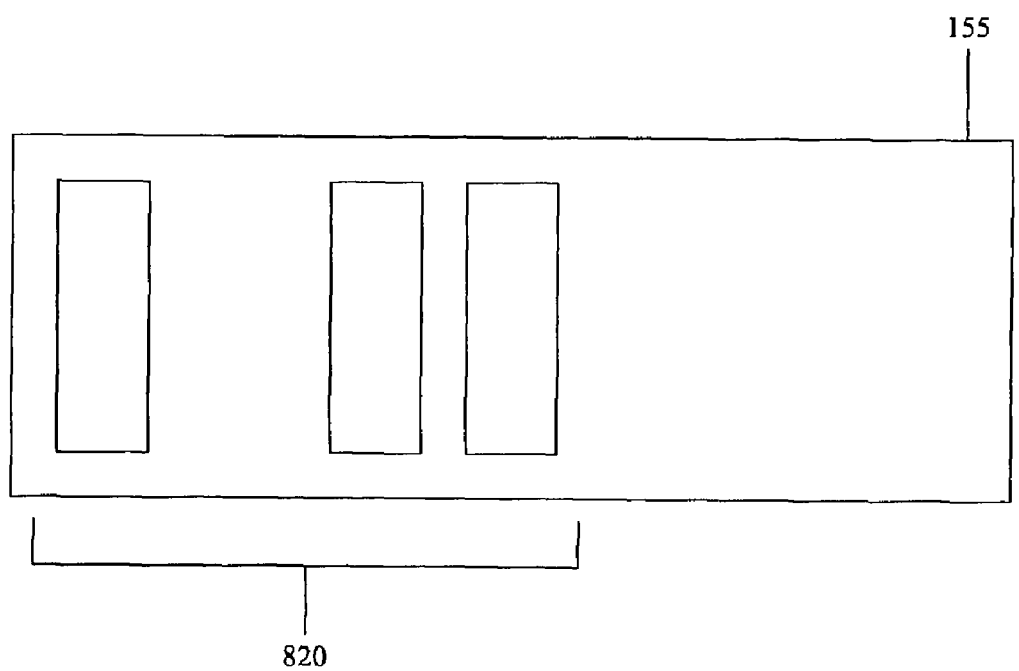
FIG. 7b shows a top view of a third exemplary pattern including coding pads that couple with the sense pads of FIG. 7a according to an exemplary embodiment of the present invention.

FIG. 7a shows a top view of sense pads 805 of the sensor array 130 according to an exemplary embodiment of the present invention. In this exemplary embodiment, the sensor array 130 includes four sense pads 805. The sense pads 805 may be disposed on a printed circuit board (PCB) 815. According to the exemplary embodiment, the sensor array 130 includes a maximum number of sense pads 805. FIG. 7b shows a top view of a third exemplary pattern 155 including coding pads 820 that couple with the sense pads 805 of FIG. 7a according to an exemplary embodiment of the present invention. As discussed above, the sensor array 130 may include the maximum number of sense pads 805. Accordingly, the pattern 155 may include coding pads 820 up to the maximum number of sense pads 805. According to the exemplary embodiment, the third pattern 155 includes three coding pads 820 (i.e., less than four, the maximum number). As illustrated, the coding pads 820 are disposed at a first, third, and fourth position, the first position being leftmost. The sense pads 805 may be, for example, conductive trances while the coding pads 820 may be, for example, metal thin film pads. The sense pads 805 may be a portion of a capacitor on its own or may be a larger capacitor when coupled to a metal pad.

Figure 8:
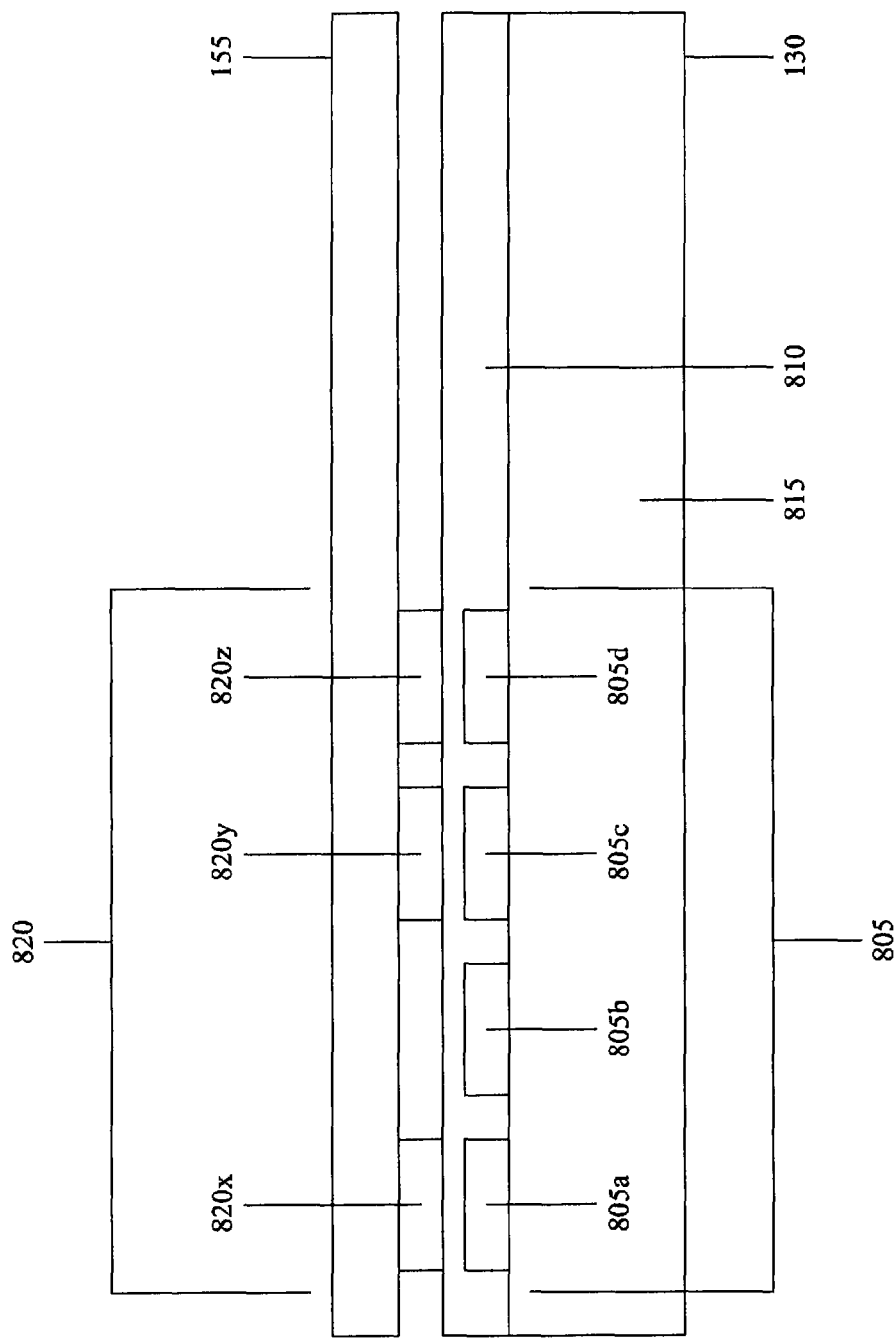
FIG. 8 shows a coupling of the sense pads of FIG. 7a with the coding pads of FIG. 7b according to an exemplary embodiment of the present invention.

FIG. 8 shows a coupling of the sense pads 805 of FIG. 7a with the coding pads 820 of FIG. 7b according to an exemplary embodiment of the present invention. As discussed above, the sense pads 805 of the sensor array 130 may be disposed on the PCB 815. FIG. 8 further illustrates that the sense pads may be covered with an insulation layer 810. The insulation layer 810 may be utilized for the capacitance measurements as well as the coupling to the coding pads 820. It should be noted that when the pattern 155 is in a proper orientation, the coding pads 820 align with a corresponding sensing pad 805.

As discussed above, the coupling of the coding pads 820 with the sensing pads 805 may provide capacitance data. According to the exemplary embodiment, the coding pads 820 may comprise coding pads 820x-z while the sensing pads 805 comprise, sensing pads 805a-d. For example, a current may be fed to the sensing pads 805 and capacitance data may be read. As illustrated, the sense pads 805a, c, and d are coupled to coding pads 820x, y, and z, respectively while sense pad 820b is non-coupled. When the sense pad 805 couples to the coding pad 820, a larger capacitor is created due to the composition of the coding pad 820 (e.g., metal thin film). The coupling/non-coupling of the sense pads 805 may be used to create a binary code. That is, coupled pads may represent a code of 1 (C1) while non-coupled pads may represent a code of 0 (C0). Thus, the exemplary embodiment of FIG. 8 may have a binary code of C1C0C1C1. This binary code may be specific to the pattern 155. Accordingly, each type of calibration storage device 150 may include a respective pattern 155 that represents a corresponding binary code. Because the sensor array in the exemplary embodiment includes four sense pads 805, a total number of binary code permutations is 16 ($2^4$). It should be noted that the sensor array 130 may include any number of sense pads. Additional sense pads may accommodate additional types of binary codes. For example, five sense pads result in 32 permutations ($2^5$), six sense pads result in 64 permutations ($2^6$), ten sense pads result in 1024 permutations ($2^{10}$), etc.

Figure 9:
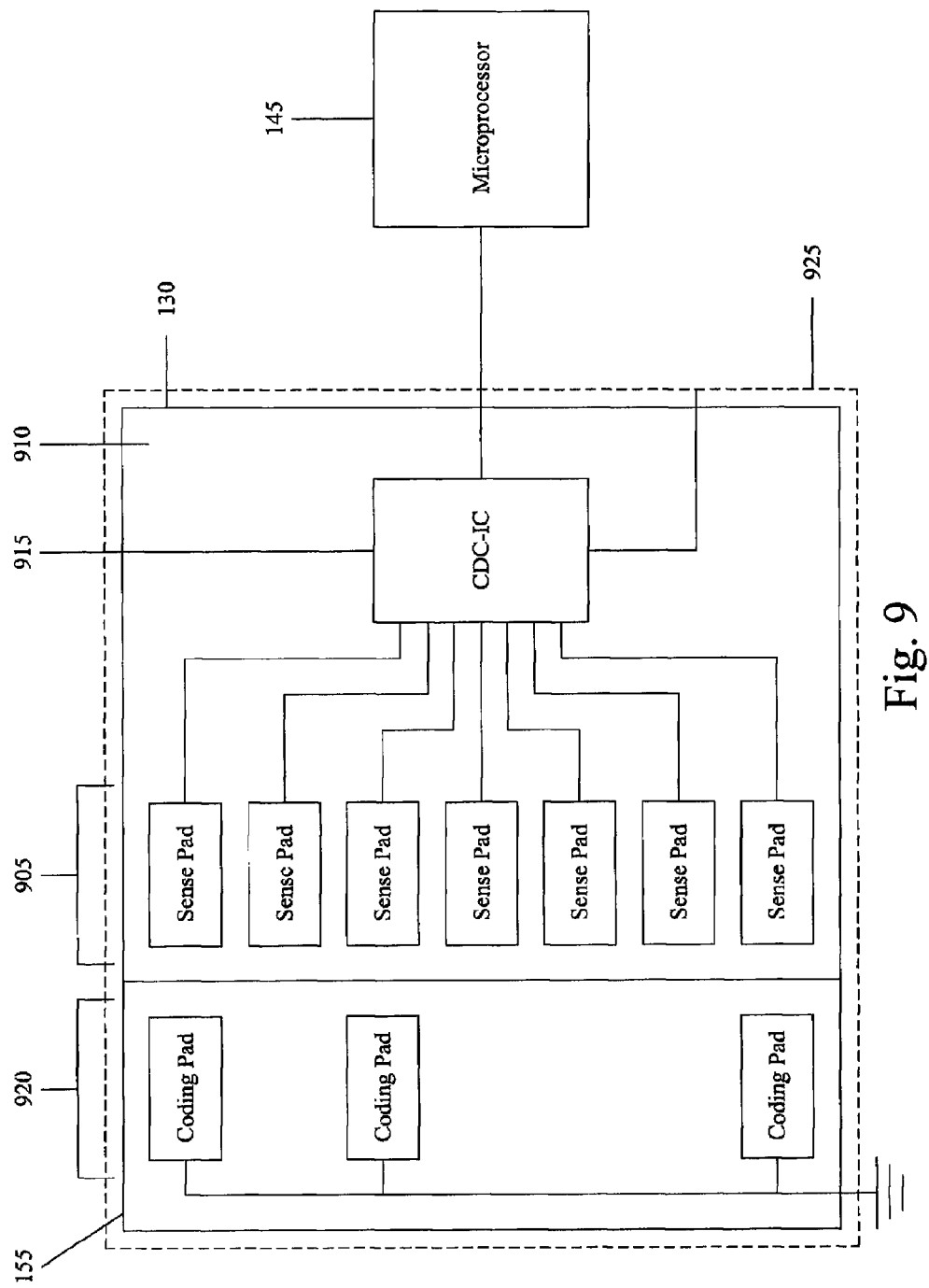
FIG. 9 shows a schematic view of another pairing substantially similar to the pairing of FIG. 8 according to an exemplary embodiment of the present invention.

FIG. 9 shows a schematic view of another pairing substantially similar to the pairing of FIG. 8 according to an exemplary embodiment of the present invention. FIG. 9 shows an exemplary embodiment of the present invention where the pattern 155 which includes three coding pads 920 that are grounded. The sensor array 130 may include seven sense pads 905 that are disposed on a PCB 910. The sense pads 905 may be formed directly on the PCB 910 when the PCB 910 already exists in the electronic device 100. Also disposed on the PCB 910 is a capacitance to digital converter integrated circuit (CDC-IC) 915. The CDC-IC 915 may receive the capacitance measurements from the sense pads 905, convert the measurements into digital form and forward them to, for example, a microprocessor 145. It should be noted that the microprocessor 145 may also be disposed on the PCB 910. Furthermore, as discussed above, the microprocessor 145 may be part of the sensor array 130, a processor of an electronic device, etc.

The CDC-IC 915 may be, for example, a model AD7142 manufactured by Analog Devices, Inc. As discussed above, the CDC-IC 915 may be connected to seven sense pads 905. Thus, there may potentially be up to 128 permutations of binary codes. Accordingly, the CDC-IC 915 may have 128 bits of resolution. In an exemplary embodiment, the CDC-IC 915 may be equipped to sense a difference of $1 \times 10^{-15}$ F capacitance change. Furthermore, the CDC-IC 915 may be equipped to automatically calibrate out environmental changes to the detection circuitry such as changes in temperature, humidity, etc. The CDC-IC 915 may also be connected to a shield 925. The shield 925 may assist in isolating the components of the sensor array 130 and the pattern 155 from interference such as electromagnetic interference (EMI), RF interference, etc.

According to the exemplary embodiment of the present invention, the CDC-IC 915 may interpret the capacitance measurements from the sense pads 905 in a variety of manners. Those skilled in the art will understand that due to outside factors (e.g., EMI, environment, etc.), a consistent capacitance measurement may not be ascertained. Because the exemplary embodiment utilizes a binary code, the capacitance measurement may be either C0 (representing a non-coupled sensor pad) or C1 (representing a coupled sensor pad with coding pad). Thus, to compensate for measurements that do not exactly correspond to the values of C0 and C1, the CDC-IC 915 may categorize any incoming measurement.

The CDC-IC 915 may categorize an incoming measurement using a deviation computation. For example, the values of C0 and C1 may be determined by a control procedure. The control procedure may determine that C0 corresponds to a minimum capacitance measurement while C1 corresponds to a maximum capacitance measurement. Those skilled in the art will understand that capacitance measurements are partially a function of temperature and humidity. Surrounding floating metals including a user close to a sense pad may thus influence the capacitance measurement. As discussed above, the CDC-IC 915 may calibrate out the interferences, utilize the shield 925, etc. The CDC-IC 915 may also classify the influences on the capacitance measurements into balk capacitance ambient value drifts. Once classified, the CDC-IC 915 may compensate for the interferences and calculate proper capacitance measurements.

In addition, even without interferences, the capacitance measurements may still not exactly correspond to the values of C0 and C1. Returning to the deviation computation, a middle value between C0 and C1 may be used as a basis of categorizing incoming capacitance measurements that are not exactly C0 or C1. The middle value may be, for example, the value of C1 less the value of C0 divided by 2 (Cm=(C1−C0)/2). It should be noted that the value of C1 is greater than the value of C0 because the sensor pad coupled to the coding pad creates a larger capacitor. An incoming capacitance measurement may be compared to the value Cm. If the measurement is less than Cm, then the measurement may be designated as C0. If the measurement is greater than or equal to Cm, then the measurement may be designated as C1. Thus, the CDC-IC 915 may interpret the capacitance measurements from each of the sense pads 905 to determine the corresponding binary code associated with the pattern 155. In the exemplary embodiment of FIG. 9, the CDC-IC 915 may determine that the pattern 155 includes a binary code of C1C0C1C0C0C0C1. The digitized code may be forwarded to the microprocessor 145 which may interpret the code to execute a proper calibration for the electronic device.

Figure 4:
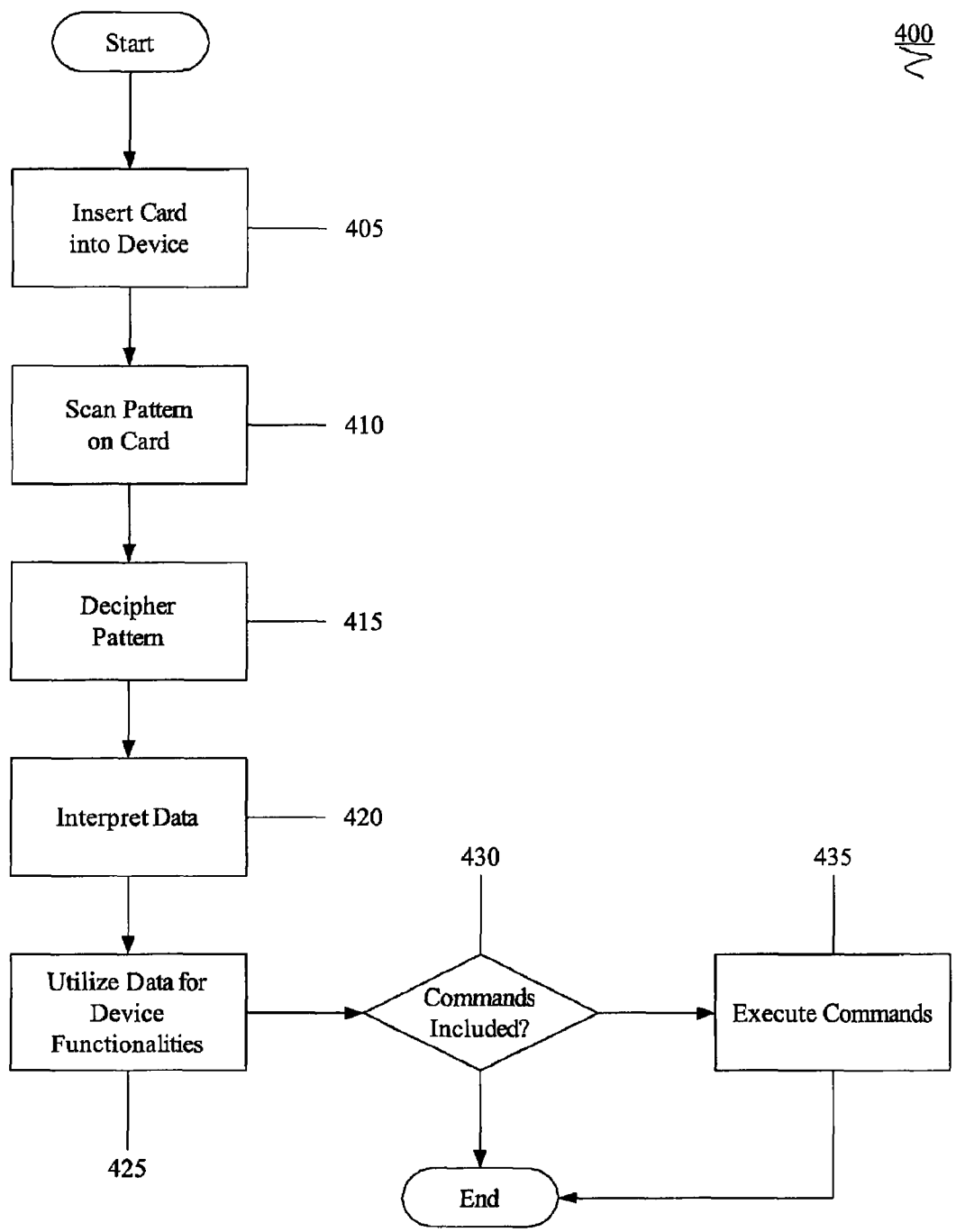
FIG. 4 shows a method of calibration according to an exemplary embodiment of the present invention.

FIG. 4 shows a method 400 of calibration according to an exemplary embodiment of the present invention. The method 400 will be described with reference to the device 100 and the calibration storage device 150 of FIGS. 1-2. The method 400 will also be described with reference to the various patterns 155a-b of FIGS. 6a-c. The method 400 utilizes the pattern 155 on the calibration storage device 150 to calibrate the device 100 in preparation to execute a functionality. As will be described in detail below, the method 400 may be used to automatically calibrate the device 100. That is, the calibration of the device 100 may be performed without a need for a separate step or adjustment. Specifically, the calibration does not require the circuitry, processor, memory, etc. of the device 100 to be separately manipulated prior to executing the functionality.

In step 405, the calibration storage device 150 is inserted into the device 100 via the port 120 by moving in the direction d. The calibration storage device 150 may be held in the recess 125. When the calibration storage device 150 is inserted in a proper orientation according to the exemplary embodiments of the present invention, the components of the calibration storage device 150 may be aligned with corresponding components of the device 100. For example, the pattern 155 may be positioned over the sensing area 135 so that the sensor array 130 may scan/read the pattern 155.

It should be noted that the calibration storage device 150 being inserted into the device 100 is only exemplary. For example, the calibration storage device 150 may be hovered or placed a distance away from the device 100. The sensing area 135 may be on a portion of the housing 105 that is not part of a recess. Thus, the area in which the calibration storage device 150 is hovered or placed may be over the sensing area 135 that is disposed partially on the housing 105.

In step 410, the pattern 155 of the calibration storage device 150 is read/scanned by the sensor array 130. As discussed above, the pattern 155 may be disposed on a bottom side of the calibration storage device 150. Consequently, the sensing array 135 may be disposed on a corresponding area within the recess 125. The sensor array 130 may read/scan the pattern 155 using, for example, capacitive measurements and/or RF measurements. The pattern 155 may include one or two-dimensional features (e.g., contrast, width, height, etc.) such as those described above with reference to the patterns 155a-b of FIGS. 6a-c. The pattern 155 may also be read using a pairing/non-pairing of sense pads and coding pads such as those described above with reference to FIGS. 7a-b, 8, and 9.

In step 415, the pattern 155 is deciphered. The pattern 155 may include parameter data that sets the device in preparation for executing a functionality. For example, the varying heights of the bars 625-633 of pattern 155b may include this data. The sensor array 130 may transmit the read/scanned pattern 155 to a processor of the device 100. It should be noted that the processor may decipher the pattern 155 from the raw data transmitted by the sensor array 130 or the sensor array 130 may be equipped to decipher the pattern 155 and transmit the deciphered data to the processor.

In step 420, the data is interpreted. As discussed above, the pattern 155 may include parameter data. The data of the pattern 155 may be interpreted to indicate that the parameter data is included. It should be noted that the data may be interpreted by the processor or by the sensor array 130. Thus, the processor may receive raw or deciphered data relating to the pattern 155 and interpret therefrom. Additionally, the sensor array 130 may be equipped to interpret the deciphered data of the pattern 155, thereby transmitting the interpreted data to the processor.

In step 425, the data is utilized for the functionalities of the device 100. If the data of the pattern 155 includes parameter data, the device 100 may utilize this data to set various parameters. For example, the calibration storage device 150 may be used for other utilities beyond providing the pattern 155, such as transmitting further data. This further data may be dependent on how the device 100 is configured. By first setting the device 100 according to the parameter data included in the pattern 155, the device 100 may be properly configured (e.g., calibrated) to receive the further data. In another example, the pattern 155 may include driver data. The driver data may be used to configure the device 100 to understand and receive the data of the calibration storage device 150 which may be another electronic device. It should be noted that the data of the calibration storage device 150 may include multiple forms of data that relate to various different functionalities.

In step 430, a determination is made whether the pattern 155 included command data. That is, the pattern 155 may further include data that indicates an action to be taken by the device 100. The command data may include, for example, an initiation of a program that is installed on the device 100. By executing the command included in the pattern 155, the device 100 may prepare to carry out a functionality related to the calibration storage device 150. If step 430 determines that command data is not included, the method 400 ends. However, if the step 430 determines that command data is included, corresponding actions are taken to execute the command data in step 435. It should be noted that, similar to the data utilized for the functionalities, multiple commands involving various functionalities may also be included.

It should be noted that the steps of the method 400 are only exemplary. Further steps may be included to expand the method 400. For example, the pattern 155 may be two-dimensional with a high density that includes a relatively large amount of data. The pattern 155 may be deciphered (i.e., step 415) and interpreted (i.e., step 420) to indicate that an initial data is utilized (i.e., step 425). Afterward, a command may be executed (i.e., step 430). Furthermore, the pattern 155 may include data that indicates a subsequent data is utilized upon executing the command. Therefore, depending on the amount of data and the types of data included in the pattern 155, additional steps may be included in the method 400.

Figure 3:
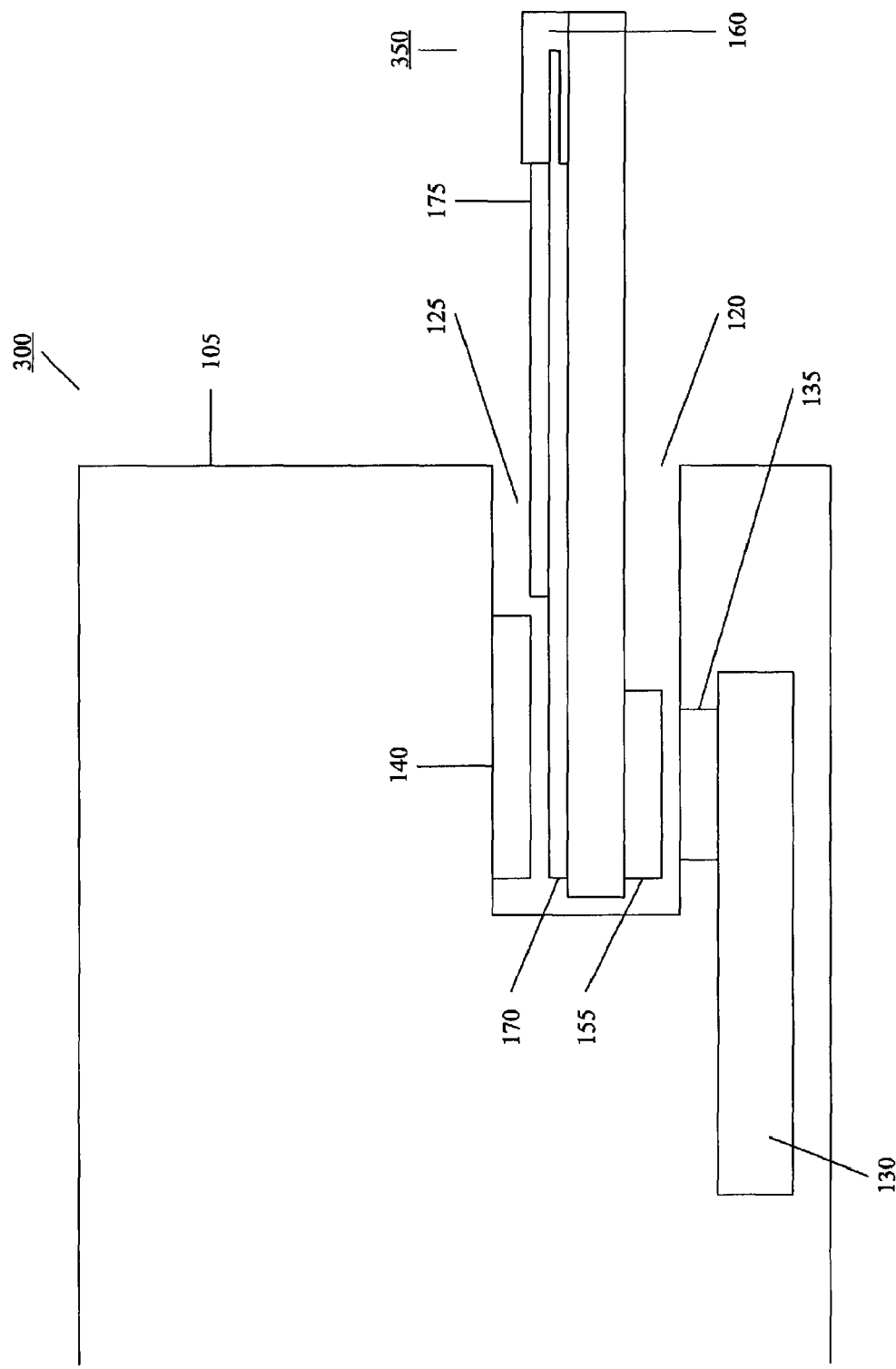
FIG. 3 shows a cross sectional view of a blood glucose meter according to an exemplary embodiment of the present invention.

FIG. 3 shows a cross sectional view of a blood glucose meter (BGM) 300 according to an exemplary embodiment of the present invention. That is, FIG. 3 illustrates a specific example in which the device 100 and calibration storage device 150 of FIGS. 1-2 may be applied. However, as discussed above, the BGM is only exemplary and the device 100 and the calibration storage device 150 may be applied to various other utilities and specimens (referred to above as "analyte"), as will be described below. In addition, as discussed above, the BGM 300 may represent an analyte meter. The BGM 300 includes substantially similar components as the device 100 of FIGS. 1-2. For example, the BGM 300 includes a housing 105, a port 120, a recess 125, a sensor array 130, and a sensing area 135. The BGM 300 further includes a connector 140. The connector 140 may be a conduit to receive data from a separate device. The connector 140 may receive data relating to a sample of blood.

FIG. 3 also shows a calibration storage device 350 according to an exemplary embodiment of the present invention. The calibration storage device 350 may be a glucose strip or strip cartridge for the BGM 300. Generally, the calibration storage device 350 may be an analyte receiving strip. The calibration storage device 350 includes substantially similar components as the calibration storage device 150 of FIGS. 1-2. For example, the calibration storage device 350 includes the pattern 155. The pattern 155 may include data such as that pertaining to specific calibration and test parameters, date of manufacture, separate whole blood and plasma calibrations, anti-counterfeiting codes, etc. The calibration storage device 350 further includes a reaction chamber 160, an electrode 170, and a lid 175. The reaction chamber 160 may be a deposit area where the sample of blood is placed. The reaction chamber 160 may include various chemicals, devices, etc. that analyze the sample of blood. The resulting data from the analysis of the sample of blood may be transmitted along the length of the calibration storage device 350 via the electrode 170. An exposed area of the electrode 170 may couple with the connector 140, thereby allowing the BGM 300 to receive the data of the blood sample. The lid 175 may be any protective layer that shields outside forces from damaging the electrode 170. The lid 175 may be, for example, glass, polymer, etc.

FIG. 10 shows a view of a fourth exemplary pattern 180 according to an exemplary embodiment of the present invention. As discussed above with reference to FIGS. 6a-c, the pattern 155 may be disposed on a bottom side of the calibration storage device 150. As illustrated in FIG. 3, the pattern 155 is also located on a bottom side of the calibration storage device 350. That is, the pattern 155 is on a side different from the electrode 170. However, as stated above and as shown in FIG. 10, the pattern 155 may be located on various other locations. FIG. 10 includes the components of the calibration storage device 350, as described above. FIG. 10 also shows a pattern 180 that is located on a same surface of the electrode 170. As illustrated, the pattern 180 may be etched onto a portion of the exposed electrode 180. Consequently, the sensing area 135 may be located on a top surface of the recess 125 corresponding to an expected disposition of the pattern 180 when in an operable position. The pattern 180 may include any of the characteristics (e.g., contrast, height, width, or a combination thereof) and may be created using any of the methods described above with reference to FIGS. 6a-c. It should be noted that the location of the pattern 180 on the electrode 170 is only exemplary. The pattern 180 may also be located on the lid 175. As a result, the sensing area 135 would also be in a corresponding location within the recess 125. For example, the sensing area 135 may be in a location closer to the port 120 relative to the connector 140. The pattern 180 may include data pertaining to specific calibration and test parameters, date of manufacture, separate whole blood and plasma calibrations, anti-counterfeiting codes, etc.

Figure 5:
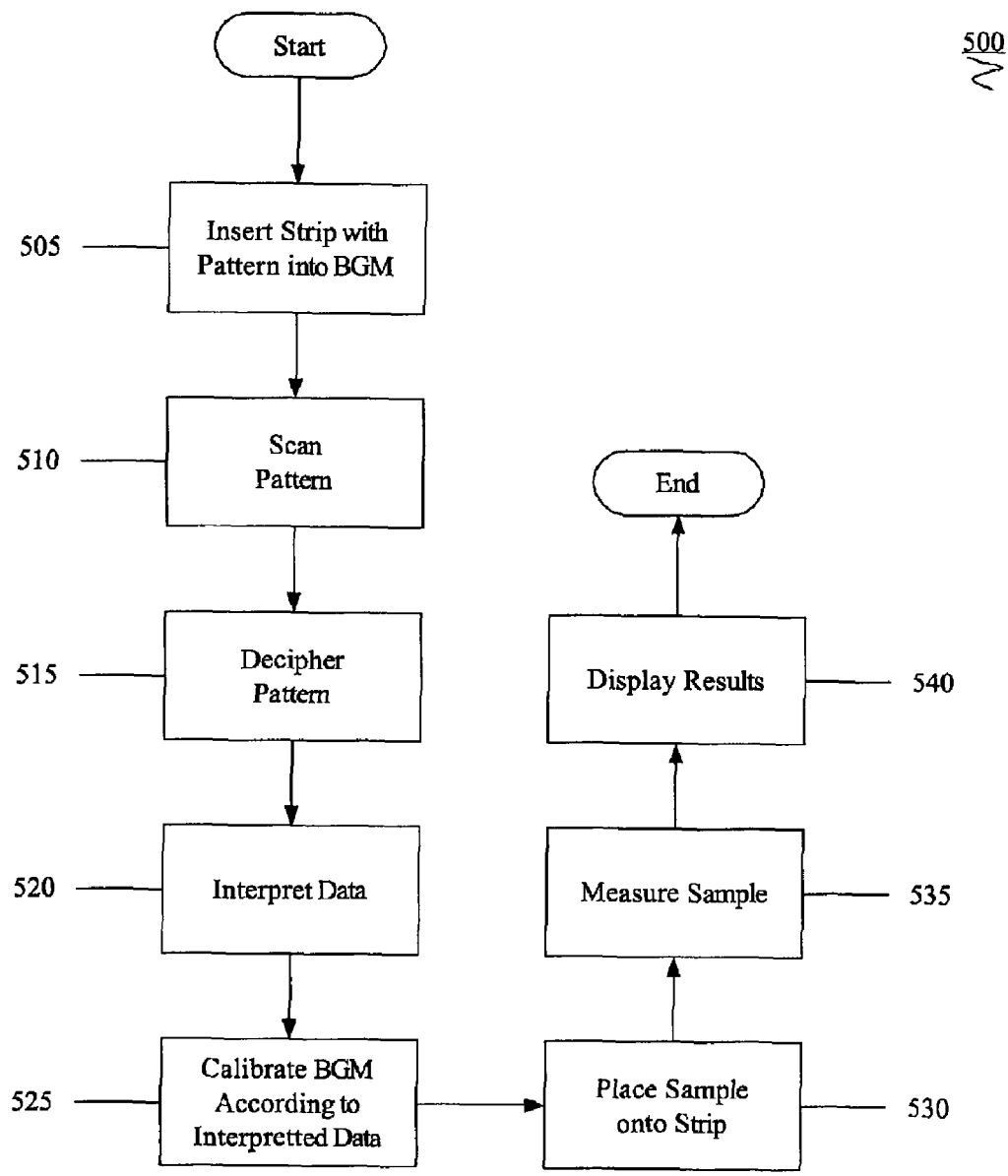
FIG. 5 shows a method of calibration for the blood glucose meter of FIG. 3.

FIG. 5 shows a method 500 of calibration for the BGM 300 of FIG. 3. The method 500 will be described with reference to the BGM 300 and the calibration storage device 350 of FIG. 3. The method 500 will also be described with reference to the various patterns 155a-b of FIGS. 6a-c and pattern 180 of FIG. 10. The method 500 utilizes the pattern 155 or 180 on the calibration storage device 350 to calibrate the BGM 300 in preparation to analyze a blood sample. That is, the BGM 300 sets parameters in preparation for receiving a blood sample depending on the type of calibration storage device 350 that is used. The calibration storage device 350 may be a test strip as described above with reference to FIG. 3.

In step 505, the calibration storage device 350 is inserted into the BGM 300 via the port 120 by moving in the direction d. The calibration storage device 350 may be held in the recess 125. According to the exemplary embodiment, the calibration storage device 350 includes an electrode end and a reaction chamber end. The electrode end includes the exposed electrode 170. The reaction chamber end includes the reaction chamber 160. Because the reaction chamber 160 is designed to receive the blood sample, the reaction chamber end of the calibration storage device 350 extends away from the device 300. Subsequently, the electrode end of the calibration storage device 350 is inserted into the recess 125 via the port 120. It should be noted that the calibration storage device 350 being inserted into the device 300 is only exemplary. The calibration storage device 350 may be hovered or placed strategically as described above with the method 400.

In step 510, the pattern 155 or 180 of the calibration storage device 350 is read/scanned by the sensor array 130. The pattern 155 may be read/scanned in a substantially similar manner as described above with reference to step 410 of the method 400. The pattern 180 of FIG. 10 may also be read in a substantially similar manner. However, as discussed above, the sensing area 135 is located in a corresponding location due to the position of the pattern 180 on the calibration storage device 350. The pattern 180 is disposed on a top surface of the calibration storage device 350 and, as a result, the sensing area 135 is located on a top surface of the recess 125.

In step 515, the pattern 155 or 180 is deciphered. In step 520, the data is interpreted. The deciphering of step 515 and the interpretation of step 520 may be performed in substantially similar manners as described above with the deciphering of step 415 and the interpretation of step 420, respectively. As described above, the pattern 155 or 180 may include data pertaining to specific calibration and test parameters, date of manufacture, separate whole blood and plasma calibrations, anti-counterfeiting codes, etc.

In step 525, the BGM 300 is calibrated according to the data included on the pattern 155 or 180. Step 425 of the method 400 described utilizing data for the functionalities of the device 100. Step 525 describes one exemplary embodiment of utilizing the data on the pattern 155 or 180 for the BGM 300. That is, the data included on the calibration storage device 350 may include parameter data. The parameter data may indicate various settings that the BGM 300 must prepare to properly interpret, receive, etc. the data for the sample of blood that will be received. That is, the BGM 300 may receive any type of calibration storage device 350 so long as the calibration storage device 350 includes the pattern 155 or 180. The calibration storage device 350 may transmit data of a blood sample in a variety of ways. Thus, calibrating the BGM 300 in a predetermined manner may allow the BGM to analyze the blood sample. It should be noted that the calibration data may be for multiple diagnostic tests to be performed on a single blood sample. For example, if the calibration storage device 350 may be used for various diagnostic tests, then the calibration data may be used to prepare the BGM to perform the various diagnostic tests.

In step 530, a blood sample is placed on the reaction chamber 160 of the calibration storage device 350. As discussed above, the reaction chamber 160 includes various chemicals that react with the deposited blood sample. Upon reaction, data may be collected pertaining to the blood sample. For example, one chemical may determine a glucose level within the blood sample. The resulting measurements may be transmitted through the electrode 170. It should be noted that the data may be transmitted through the electrode 170 in a variety of manners. For example, the calibration storage device 350 may include a power supply and circuitry and electrically forwards the data. In another example, the electrode may include chemical indicators that function in conjunction with the reaction chamber 160. The chemical indicators may be used as a gauge to determine various criteria relating to the blood sample.

In step 535, the blood sample is measured. The measurement of the blood sample may be performed upon the determining the data from the reaction chamber 160, the electrode 170, or a combination thereof. The connector 140 may serve to couple the calibration storage device 350 with the device 300, thereby allowing a transmittal of the data from the calibration storage device 350 to the device 300. It should be noted that the measurement of the blood sample may be performed by components of the calibration storage device 350, the processor of the device 300, a measuring component (not shown) of the device 300, etc. In step 540, the results of the analysis of the blood sample is displayed. For example, the results may include a blood sugar concentration, blood type, red cell count, etc. The results may be displayed using, for example, the display 110.

It should be noted that the step of the method 500 are only exemplary. The method 500 may include further steps. For example, similar to the method 400, the calibration storage device 350 may include commands for the BGM 300 to execute. The pattern 155 or 180 may include commands that the BGM 300 must execute in order to properly analyze the incoming data for the blood sample. The commands may pertain to, for example, executing a program that is required to analyze a blood sample placed on a type of calibration storage device 350. In another example, the BGM 300 may initially be deactivated with only the sensing area 135 active. When the sensing area 135 detects the pattern 155 or 180, the BGM 300 may activate and proceed with the method 500.

It should again be noted that the present invention described with reference to the BGM 300 is only exemplary. The present invention may be used in a variety of utilities. For example, the calibration storage device 150 may be an identification calibration storage device. The pattern 155 may be a unique one or two-dimensional sequence respective of a user of the device 100. That is, when the calibration storage device 150 is inserted into the device 100, the sensing array 130 may read/scan the pattern 155 to determine if an authorized user has activated the device 100. In another example, the calibration storage device 150 may be an installation calibration storage device. The pattern 155 may include a set of instructions for the device 100 to follow. Upon following the instructions, the device 100 may be capable of performing additional functionalities that correspond to the data included in the pattern 155. In yet another example, the calibration storage device 150 may include decryption codes. The data, commands, instructions, etc. of the calibration storage device 150 may be encrypted. Thus, when the device 100 reads/scans the pattern 155, the device 100 learns a decryption method to read the data of the calibration storage device 150.

It should also be noted that the pattern 155 or 180 may be encrypted. Therefore, only a device equipped to decrypt the pattern 155 or 180 may utilize the functionalities related to the calibration storage device 150.

The exemplary embodiments of the present invention allow a simple and lost cost electrical read technology for calibrating an electronic device. One exemplary advantage of the exemplary embodiments of the present invention is the elimination of a physical, conducting electrical contact often necessary to calibrate an electronic device. For example, a separate computing device may be required to electrically connect to the electronic device in order to perform a proper calibration. Furthermore, this electrical connection may entail an unnecessarily invasive disassembly of the electronic device. Another exemplary advantage of the exemplary embodiments of the present invention is a low production cost of the label for calibration in comparison to currently used calibration methods. The exemplary embodiments of the present invention only require the sensor array and label to properly calibrate the electronic device. Various electronic devices may already be equipped with the sensor array. Therefore, manufacturing of the label may be the only requirement. The label itself may be inexpensively made, depending on the amount of data required to be encoded therein. Yet another exemplary advantage of the exemplary embodiments of the present invention is that the label and data encoded therein may be retrofitted with any existing manufacturing technologies or electronic devices. For example, the label may be separately manufactured and may be affixed to the calibration storage device (e.g., glucose strip, strip cartridge, etc.). The electronic device may also electrically connect to an external sensor array to scan the label, thereby calibrating the electronic device.

It will be apparent to those skilled in the art that various modifications may be made in the present invention, without departing from the spirit or scope of the invention. Thus, it is intended that the present invention cover the modifications and variations of this invention provided they come within the scope of the appended claims and their equivalents.

What is claimed is:

1. A device, comprising:
   a sensor array collecting data from a pattern based on a capacitive measurement, the pattern being included on a calibration storage device, the pattern including a plurality of variations of at least one of height, width, and contrast; and
   a processor receiving the data from the sensor array and calibrating the device in accordance with the data.

2. The device of claim 1, wherein the calibrating includes preparing the device to perform a functionality in conjunction with the calibration storage device.

3. The device of claim 2, wherein the functionality is a diagnostic test on a sample received by the calibration storage device.

4. The device of claim 3, wherein the diagnostic test includes testing an analyte of the sample, the calibration storage device being an analyte receiving strip.

5. The device of claim 1, further comprising:
   a port receiving and aligning the calibration storage device for the sensor array to collect the data from the pattern.

6. The device of claim 1, wherein the sensor array is external to a housing of the device and is coupled to the device via a connector.

7. The device of claim 1, wherein the data includes command data, the command data indicating at least one command to be executed by the device.

8. The device of claim 1, wherein the pattern is at least one of a one-dimensional and two-dimensional sequence.

9. The device of claim 8, wherein the pattern is a two-dimensional sequence and wherein the sensor array is one-dimensional, the sensor array reads the pattern as it is slid past.

10. The device of claim 1, wherein the sensor array includes a plurality of sense pads and the pattern includes at least one coding feature so that, when in a proper orientation, the at least one coding feature associates with at least one of the plurality of sense pads.

11. The device of claim 10, wherein a sense pad associated with one of the at least one coding feature creates a first capacitance while a sense pad unassociated with one of the at least one coding feature creates a second capacitance, so that the capacitive measurement creates an ordered list of values from each of the plurality of sense pads, each value corresponding to one of the first capacitance and the second capacitance.

12. The device of claim 10, wherein the plurality of sense pads are disposed on an existing printed circuit board of the device.

13. The device of claim 10, further comprising:
   a heterogeneous dielectric cover disposed over the plurality of sense pads, the heterogeneous dielectric cover patterned to enhance data recovery by concentrating electric field lines.

14. A method, comprising:
   reading a pattern using a capacitive measurement, the pattern being included on a calibration storage device, the pattern includes a plurality of variations of at least one of height, width, and contrast;
   determining data included in the pattern; and
   calibrating a device in accordance with the data, wherein the calibrating includes preparing the device to perform a functionality in conjunction with the calibration storage device.

15. The method of claim 14, wherein the functionality is a diagnostic test on a sample received by the calibration storage device.

16. The method of claim 14, further comprising:
   executing commands on the device, the commands included in the data of the pattern.

17. The method of claim 14, wherein the pattern is at least one of a one-dimensional and two-dimensional sequence.

18. The method of claim 17, further comprising:
   wherein the pattern is the two-dimensional sequence, and further including sliding the two-dimensional sequence past a one-dimensional sensor array to read the two-dimensional sequence.

19. The method of claim 14, further comprising:
   wherein the pattern is read by a sensor array, the sensor array including a plurality of sense pads and the pattern including at least one coding feature, associating each of the at least one coding feature to one of the plurality of sense pads.

20. The method of claim 19, further comprising:
   when a sense pad associated with one of the at least one coding feature creates a first capacitance while a sense pad unassociated with one of the at least one coding feature creates a second capacitance, representing the capacitive measurement as an ordered list of values from each of the plurality of sense pads, each value corresponding to one of the first capacitance and the second capacitance.

21. The method of claim 19, wherein the plurality of sense pads are disposed on an existing printed circuit board of the device.

22. The method of claim 19, further comprising:
patterning a heterogeneous dielectric cover disposed over the plurality of sense pads to concentrate electric field lines, thereby enhancing data recovery.

23. A method, comprising:
receiving, by an analyte meter, an analyte receiving strip;
reading a pattern disposed on the analyte receiving strip using a capacitive measurement, the pattern including a plurality of variations of at least one of height, width, and contrast;
determining calibration data included in the pattern;
calibrating the analyte meter in accordance with the calibration data;
receiving an analyte on the analyte receiving strip;
analyzing the analyte using the calibrated analyte meter; and
displaying results of the analysis.

24. The method of claim 23, wherein the calibration data includes at least one of test parameters, a date of manufacture of the analyte receiving strip, a whole blood parameter, a plasma parameter, an anti-counterfeiting code, commercial data, regional identification data, and software control data.

25. A method of determining an analyte concentration of a fluid sample, the method comprising:
providing a test strip including a pattern disposed thereon and a channel formed therein, the pattern including a plurality of variations of at least one of height, width, and contrast;
providing an analyte meter including a port;
placing the test strip into the port of the analyte meter;
reading the pattern using a capacitive measurement;
determining calibration data using the capacitive measurement of the pattern;
placing a fluid sample in the channel of the test strip; and
determining the analyte concentration of the fluid sample using the calibration data.

26. A method of determining an analyte concentration of a fluid sample, the method comprising:
providing a test strip including a pattern disposed thereon and a channel formed therein, the pattern including a plurality of variations of at least one of height, width, and contrast;
providing an analyte meter including a port;
placing the test strip into the port of the analyte meter;
reading the pattern using a radio frequency measurement;
determining calibration data using the radio frequency measurement of the pattern;
placing a fluid sample in the channel of the test strip; and
determining the analyte concentration of the fluid sample using the calibration data.

* * * * *